United States Patent [19]

Dean et al.

[11] Patent Number: 4,604,096
[45] Date of Patent: Aug. 5, 1986

[54] DISPOSABLE DIAPER WITH INTEGRAL DISPOSAL SYSTEM

[75] Inventors: Raymond S. Dean, Medford; William A. Barabino, North Reading, both of Mass.

[73] Assignee: Physiological Research Associates, N. Reading, Mass.

[21] Appl. No.: 770,226

[22] Filed: Aug. 26, 1985

[51] Int. Cl.⁴ .............................................. A61F 13/16
[52] U.S. Cl. ................................................. 604/385 A
[58] Field of Search ............... 604/385, 389, 392, 394, 604/397, 398

[56] References Cited

U.S. PATENT DOCUMENTS

| | | | |
|---|---|---|---|
| 3,274,999 | 9/1966 | Robinson | 604/385 |
| 3,369,545 | 2/1968 | Wanberg | 604/385 |
| 4,430,087 | 2/1984 | Azpiri | 604/385 |

*Primary Examiner*—John D. Yasko
*Attorney, Agent, or Firm*—Joseph S. Iandiorio

[57] ABSTRACT

A diaper assembly with integral disposal system, including a disposable diaper and an envelope integrally carried on the outside of the diaper, that has a mouth for receiving the diaper when soiled. One or more elements engage a section of the diaper with another section of the diaper to secure it on a wearer in a use configuration and restrict the mouth of the envelope in a disposal configuration.

20 Claims, 6 Drawing Figures

DISPOSABLE DIAPER WITH INTEGRAL DISPOSAL SYSTEM

FIELD OF INVENTION

This invention relates to an integral disposal system for a disposable diaper, and more particularly to such a system which secures the diaper in position on a wearer and later encloses the diaper for considerate disposal.

BACKGROUND OF INVENTION

Presently, considerable disposal of a diaper is difficult. A used reusable cotton diaper is handled during and after changing and then is placed in a container. Typically, the initial container is a nursery diaper pail which accumulates diapers over time. The diapers are later washed for re-use.

To avoid the chore of washing the used cotton diaper, disposable diapers are designed to be used once and discarded. However, the disposable diaper shares the same initial problems as does the reusable cotton diaper: the disposable diaper must still be handled during and after changing and must be placed in an initial container or simply discarded into a waste receptacle, particularly if the change occurs away from home.

Improvements in disposable diapers have been in the areas of absorbency, softness and comfort-fit; the problem of considerate disposal of the used diaper is rarely addressed. Temporary storage in a diaper pail rapidly results in the development of disagreeable odors such as the odor of ammonia. Transport of the used diaper to a collection facility is awkward, particularly in a public place.

Some have attempted to address the problem of considerate disposal by manufacturing individual diaper disposal bags. These bags are wholly separate from the disposable diaper and can be inadvertantly left behind during travels away from home. Further, there is no assurance that a nursery will be equipped with the same number of disposable bags as the number of diapers.

SUMMARY OF INVENTION

It is therefore an object of this invention to provide a disposable diaper which has an integral disposal system.

It is a further object of this invention to provide such a disposal system which is clean and convenient.

A still further object of this invention to provide such a disposal system which also secures the diaper in position on a wearer.

Yet another object of this invention is to provide such a disposal system which inhibits the emanation of ammonia and other undesirable odors from a used diaper.

It is a further object of this invention to provide such a disposal system which inhibits the development of undesirable odors in a nursery diaper pail or other container.

This invention features a diaper assembly with integral disposal system including a disposable diaper and an envelope integrally carried on the outside of the diaper and a mouth for receiving the diaper when it is soiled. There are also means for engaging a section of the diaper with another section of the diaper to secure the diaper on a wearer in a use configuration and restricting the mouth of the envelope in a disposal configuration.

In one embodiment, the envelope has defined on it a rim surrounding the mouth and is swingably fixed along a portion of the rim to the diaper. Alternatively, the envelope is carried by a protective covering which overlies the envelope in the use configuration. The means for engaging may include at least one adhesive tab mounted on a section of the diaper or strap means having at least one free end and adhesive means mounted proximate the free end of the strap means. Alternatively, the means for engaging includes strap means for securing sections of the diaper in the use configuration and restricting the mouth of the diaper in the disposal configuration. The diaper assembly may further include removable cleansing means disposed within said envelope in the use configuration.

The invention may be expressed as a diaper assembly which has a diaper having an outer line on which are defined a first section and a second section, the second section having a first area, and an envelope which has a mouth, the envelope having defined on it a rim surrounding the mouth and being swingably fixed along a portion of the rim to the first area of the diaper. The envelope is of sufficient size to accommodate the diaper in a disposal configuration and the mouth of the envelope is sufficiently large to accept the diaper when it is swingably positioned in the envelope. There are also strap means having a free end for securing the second section to the first section to position the diaper on a wearer in a use configuration and restricting the mouth of the envelope in the disposal configuration. The diaper assembly also includes adhesive means mounted on the strap means proximate the free end for affixing the free end to the first section of the diaper in the use configuration and to the envelope in the disposal configuration.

In a preferred embodiment, the second section of the diaper further includes a second area and the envelope has an attachment region which is removably attached to the second area of the diaper in the use configuration. The envelope includes means, disposed on the rim opposite the fixed portion, for guiding the strap means during restriction of the mouth of the envelope in the disposal configuration. The means for guiding may be an opening in the rim of the envelope. The portion of the rim of the envelope which is fixed to the first area of the diaper may be a portion of the interior surface of the rim. The portion of the strap means opposite to the free end may be fixed to the rim of the envelope or to the first area of the diaper. The strap means may have at least two free ends and the envelope may include means, on either side of the fixed portion of the rim, for receiving each free end of the strap means; the means for receiving may include at least one slit in the envelope on either side of the fixed portion.

In one embodiment, the first area is located in the region of the diaper that is positionable near the waist of the wearer, the first section is the front of the diaper and the second section is the back of the diaper. The diaper assembly may further include a protective covering which overlies at least a portion of the envelope to restrict inadvertent movement of the envelope in the use configuration.

DISCLOSURE OF PREFERRED EMBODIMENT

Other objects, features and advantages will occur from the following description of a preferred embodiment and the accompanying drawings, in which.

This invention may be accomplished by a disposable diaper which integrally carries an envelope for receiving the diaper when soiled. One or more elements are associated with the diaper for engaging one section of the diaper to another section to secure the diaper in use on a wearer and for restricting the mouth of the envelope after the soiled diaper is placed into the envelope. In one construction, the envelope is swingably attached to the diaper. In another construction, one or more adhesive tabs attach together the sections of the diaper in use and one or more closure elements restrict the mouth for considerable disposal. In yet another construction, at least one dual-function strap secures the diaper on a wearer and seals the envelope after the used diaper is swingably positioned into the envelope.

To inhibit inadvertent movement of the envelope, another portion of the envelope may be temporarily attached to the diaper until it is detached before the diaper is moved into the envelope. Alternatively, a protective covering is provided for the envelope to restrict movement of the latter until considerate disposal is desired.

Figure 1:
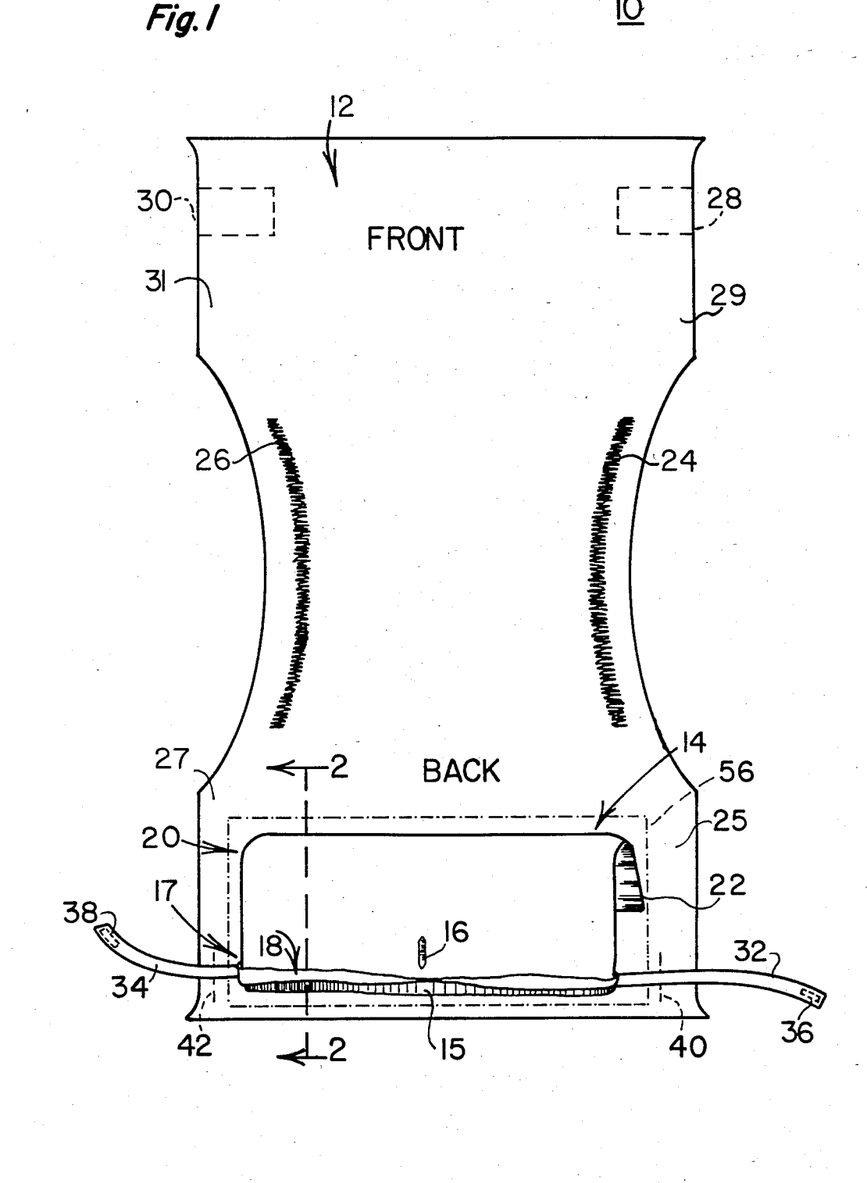
FIG. 1 is a top plan view of a disposable diaper with integral straps and an envelope carried by the diaper.

Diaper assembly 10, FIG. 1, includes disposable diaper 12 on which is positioned envelope 14. Diaper 12 has a front section and a back section, labelled FRONT and BACK, respectively, on the outside of diaper 12; preferably, envelope 14 is mounted on the back section as indicated in FIG. 1. The back section has first area 17 to which the underside of rim 18 is attached. The back area has second area 20 to which lower portion 22 of envelope 14 is removably attached. Lower portion 22 is attached by sear-fastening when it and the outer surface of diaper 12 are composed of plastic material. Otherwise, an adhesive such as an epoxy is used.

Envelope 14 includes mouth 15 and guide opening 16 in rim 18. Opening 16 guides straps 32, 34 during the restriction of mouth 15 to provide a disposal configuration for diaper assembly 10 as described below. Acceptable materials for envelope 14 and straps 32, 34 are plastics similar to the conventional outer line of diaper 12.

Diaper 12 includes conventional elastic material 24, 26 which serves to gather the sides of diaper 12 about the thighs of the wearer. Conventional diapers directly attach flaps 29, 31 of the back section to flaps 25, 27 of the front section using adhesive tabs 28, 30, shown in phantom. In one embodiment, a diaper assembly according to this invention utilizes tabs 28, 30 to engage flaps 25, 27 while straps 32, 34 are used to restrict mouth 15 in the disposal configuration. Instead of utilizing adhesive tabs 28, 30, however, diaper assembly 10 is secured in position on a wearer utilizing dual-function straps 32, 34 having adhesive material 36, 38 positioned respectively on their free ends. As described below, straps 32, 34 are affixed at the ends opposite their free ends to the inside of envelope 14 and emerge from either side, as shown in FIG. 1. Alternatively, straps 32, 34 can underlie one or more layers of diaper 12 and emerge through slits 40, 42, shown in phantom. Straps 32, 34 provide greater security and adjustability than that provided by conventional tabs 28, 30.

Figure 2:
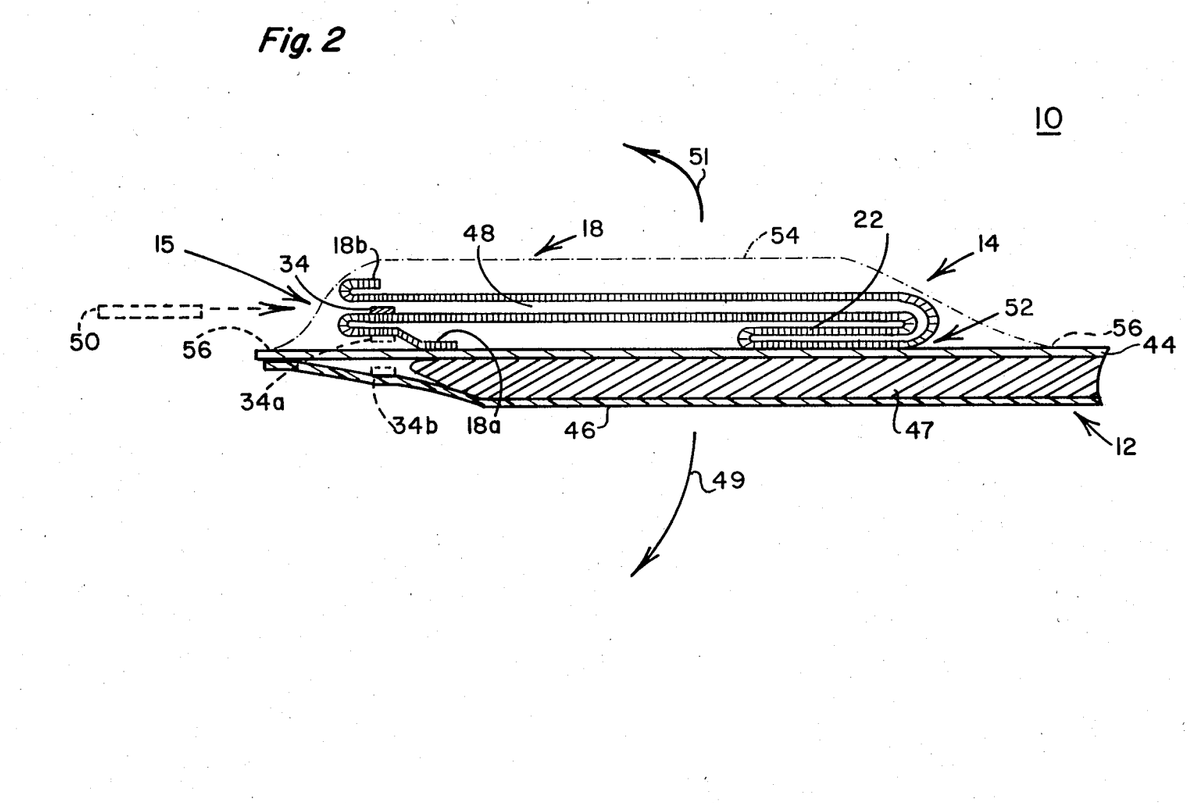
FIG. 2 is a cross-sectional view of FIG. 1 along the line 2—2.

As shown in FIG. 2, strap 34 is attached to the interior portion of rim 18. Alternatively, strap 34 can be located as indicated by position 34a between envelope 14 and outer liner 44 of diaper 12. In yet another embodiment, the strap is located in position 34b between outer liner 44 and inner absorbent lining 46 next to absorbent pad 47. Also, it is readily apparent that straps 32 and 34 can be composed of a single piece of material running underneath envelope 14 and emerging at either side.

The term "rim", such as rim 18, includes the generous border surrounding mouth 15. While the rim can be formed from reinforced material, rim 18 of FIGS. 1 and 2 is simply a border that is defined on envelope 14. Rim 18 includes underlying portion 18a which is permanently attached to liner 44 and upper portion 18b which is simply folded upon itself. As shown in FIG. 1, rim 18 is not folded upon itself in the vicinity of opening 16 but increasingly folds upon itself as it approaches the underside of envelope 14. As shown in FIG. 2, the width of folded-over portion or tuck 18b approaches the tuck shown as portion 18a; the width of tuck 18a against outer liner 44 remains generally the same throughout its length bordering mouth 15. The advantage of this arrangement is described in relation to FIGS. 4–6 below.

Compartment 48 of envelope 14 can be used for storing cleansing material 50, shown in phantom, which is stored in compartment 48 before and during use of diaper assembly 10 and for cleansing the wearer of diaper assembly 10 after use. Cleansing material 50 preferably is a biodegradable Handi-Wipe-type material or similarly moisturized tissue which may be stored in envelope 14 which of itself acts as an inhibitor of evaporation. Alternatively, the moisturized tissue is sealed in a foil wrap.

Lower portion 22 of envelope 14 is lightly sear-fastened at attachment region 52 to outer plasticized liner 44. Attachment region 52 serves to minimize the bulk of envelope 14 and to restrict its movement while diaper assembly 10 is worn in a use configuration. In preparation for considerate disposal, envelope 14 is pull-separated from and swingably positioned relative to diaper 12 as indicated by arrows 49, 51.

To further restrict inadverent movement of envelope 14 during the use configuration, the inner portion of rim 18b can be lightly fastened to strap 34 or to rim 18a, such as by conventional sear-fastening or electrostatic adhesion. Also, protective covering 54 can be provided to overlie at least a portion of envelope 14, especially proximate lower portion 22. Protective covering 54, such as a sheet of opaque plastic, can be attached to outer liner 44 to surround envelope 14 such as illustrated by attachment locus 56, FIGS. 1 and 2. Openings in covering 54 are provided for straps 32, 34. Outer covering 54 can form a "blister" which integrally associates envelope 14 with diaper 12 even if the former is not otherwise attached. Covering 54 is easily ruptured to free envelope 14 after diaper 12 becomes soiled.

Figure 3:
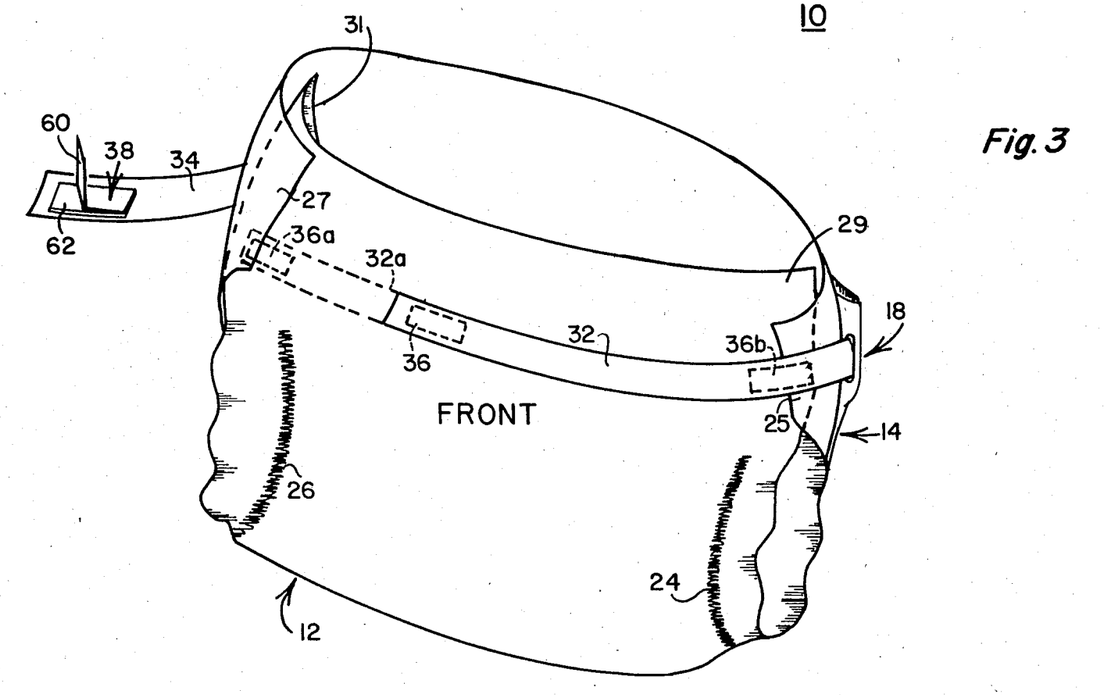
FIG. 3 is an axonometric view of the diaper assembly of FIG. 1 being secured in the use configuration.

Diaper assembly 10 is positioned in the use configuration about a wearer as shown in FIG. 3. As viewed from the front, flaps 25, 27 of the back section are brought around and over flaps 29, 31 of the front section. Adhesive material 36, 38 is prepared by exposing an adhesive surface, such as by removing protective covering 60 from adhesive pad 62, e.g., similar to the material of conventional adhesive tabs 28, 30, FIG. 1. Straps 32, 34, carrying flaps 25, 27, are thereby attached to the front section. Alternatively, a single strap can be used, such as strap 32a, FIG. 3, shown in phantom extending across the front section and onto flap 27; in that embodiment, strap 34 is not required. Additional adhesive material can be provided such as material 36a and 36b, shown in phantom. Rim 18 is positioned near the waist of the wearer; envelope 14 is carried on the back section of diaper 12.

Figure 4:
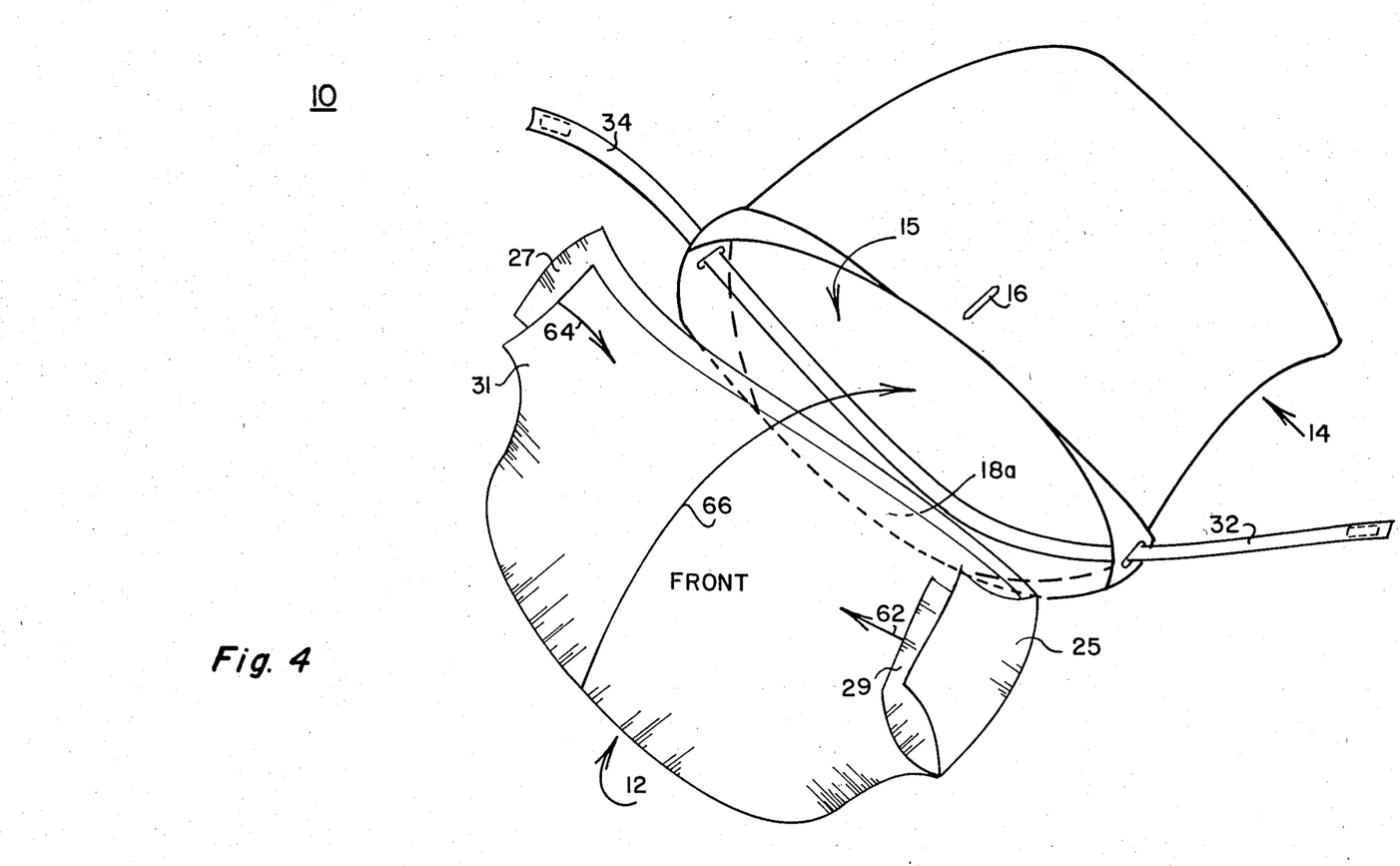
FIG. 4 is an axonometric view of the diaper assembly of FIG. 3 approaching the disposal configuration as the diaper is folded and inserted into the expanded envelope.
Figure 5:
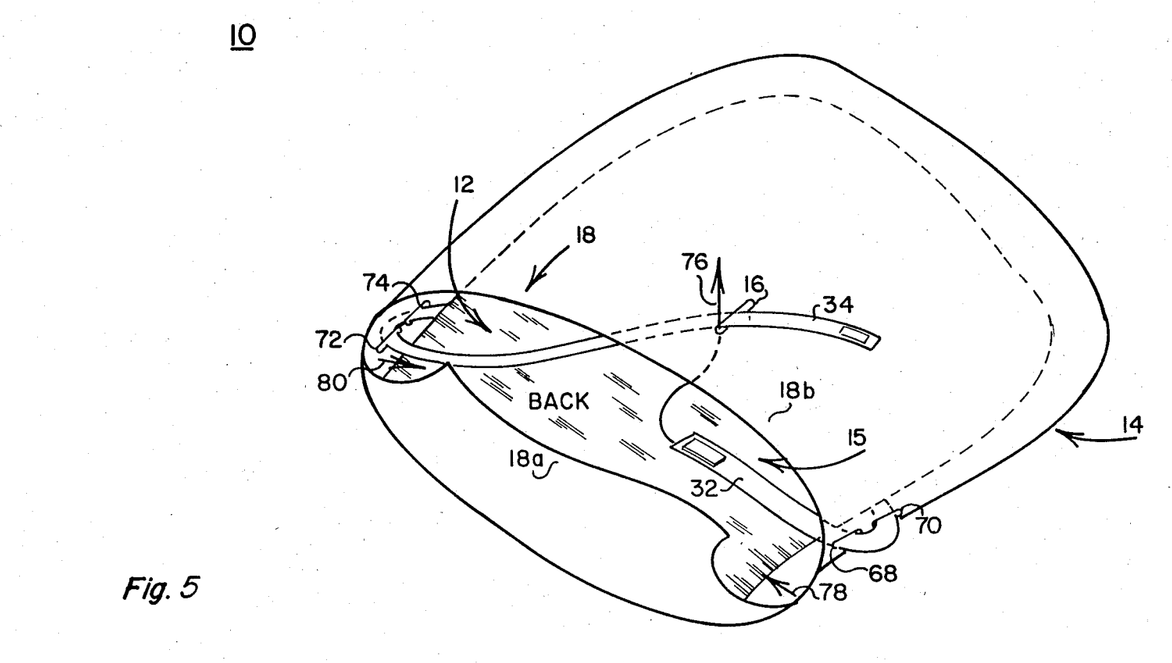
FIG. 5 is an axonometric view of the diaper assembly of FIG. 4 after it is inserted into the envelope.
Figure 6:
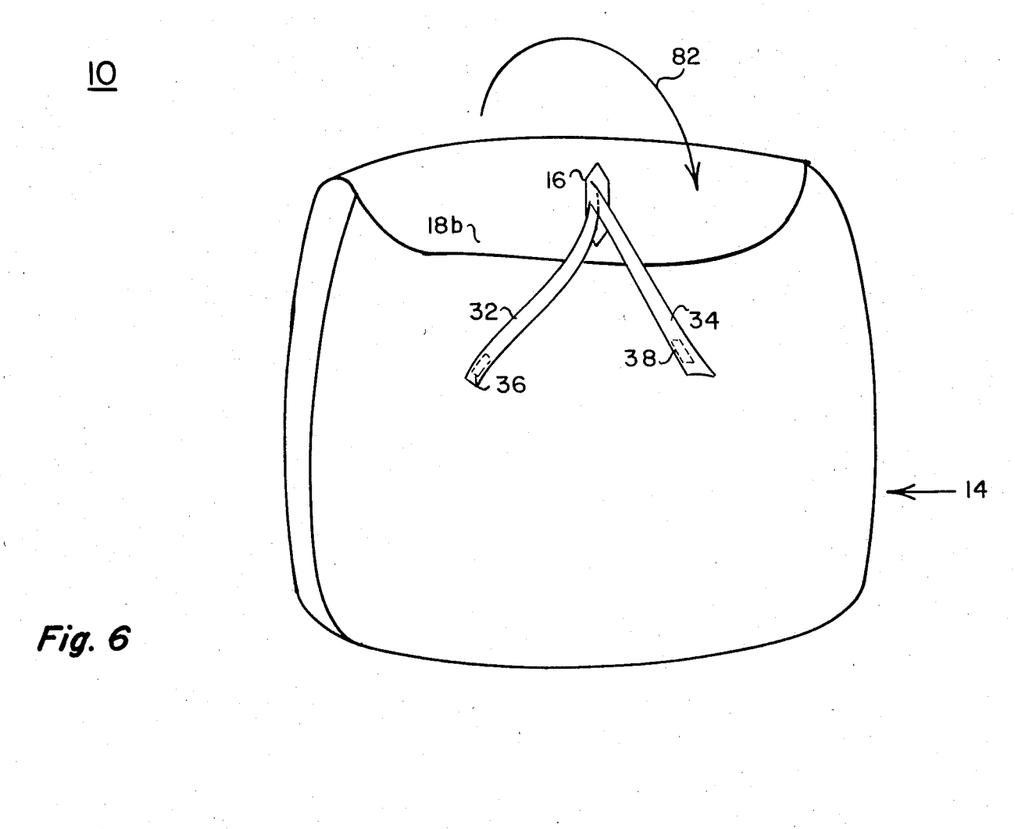
FIG. 6 is an axonometric view of the diaper assembly of FIG. 5 in the disposal configuration.

During changing of diaper assembly 10 after diaper 12 becomes soiled, diaper 12 is prepared for considerate disposal as shown in FIGS. 4–6. As shown in FIG. 4, the front section of diaper 12 is half-folded onto the inside of the back section and then flaps 25, 29 are folded onto the outside of the front section of diaper 12 as indicated by arrow 62, while flaps 27, 31 are folded as indicated by arrow 64. Envelope 14 is shown detached from the back section of diaper 12; attached rim portion 18a is indicated in phantom beneath diaper 12. Diaper 12 is then swung through mouth 15 into envelope 14 as shown by arrow 66.

Straps 32, 34 are brought through opening 16 as shown in FIG. 5. Rim 18 is illustrated as wholly unfolded to reveal slits 68, 70 in rim 18 through which passes strap 32, and slits 72, 74 which receive strap 34.

After strap 32 is fed through opening 16, arrow 76, it is pulled to bring rim 18 inward, as indicated by arrow 78. Similarly, strap 34 is tightened to draw in the opposite portion of rim 18 as shown by arrow 80.

The advantage of attaching an inner portion of rim 18 as rim portion 18a is best shown in FIGS. 5 and 6. As diaper 12 is folded inside envelope 14, rim portion 18a covers much of the exposed portion of diaper 12 proximate mouth 15. As the opposite sides of rim 18 are drawn inward, arrows 78, 80, FIG. 5, and the rim portion 18 opposite rim portion 18a is drawn over the top of portion 18a as indicated by arrow 82, FIG. 6, diaper 12 becomes wholly enclosed within envelope 14. Adhesive pads 36 and 38, exposed initially to assist the securing of diaper assembly 10 in the use configuration, now attach to the outside of envelope 14 to secure rim portion 18b in the disposal configuration.

Straps 32, 34 are shown above passing through and guided by opening 16 and slits 68, 70 and 72, 74 in rim 18. However, this is not a limitation for a diaper assembly according to this invention. The same guiding functions can be provided by a loop or ring of material. Alternatively, rim 18 may lack guides entirely for the disposal configuration and, after the rim is gathered to restrict the mouth, one or more straps are simply positioned over the gathered material and attached using adhesive material. Further, if separate adhesive tabs 28, 30, FIG. 1, are used to secure diaper 12 on a wearer, straps 32,34 can be replaced by any other closure element, such as a string or a piece of adhesive carried by the diaper assembly, for restricting the mouth in the disposal configuration.

Although specific features of the invention are shown in some drawings and not in others this is for convenience only as each feature may be combined with any or all of the other features in accordance with the invention.

Other embodiments will occur to those skilled in the art and are within the following claims:

What is claimed is:

1. A diaper assembly with integral disposal system, comprising:
   a disposable diaper;
   an envelope integrally carried on the outside of said diaper and having a mouth for receiving said diaper when soiled; and
   strap means for engaging a section of said diaper with another section of said diaper to secure said diaper on a wearer in a use configuration and restricting the mouth of said envelope in a disposal configuration.

2. The diaper assembly of claim 1 in which said envelope has defined on it a rim surrounding the mouth and is swingably fixed along a portion of the rim to said diaper.

3. The diaper assembly of claim 1 in which said envelope is carried by a protective covering which overlies said envelope in the use configuration.

4. The diaper assembly of claim 1 further including removable cleansing means disposed within said envelope in the use configuration.

5. A diaper assembly with integral disposal devices, comprising:
   a diaper having an outer liner on which is defined a first section and a second section, the second section having a first area;
   an envelope which has a mouth, said envelope having defined on it a rim surrounding the mouth and being swingably fixed along a portion of the rim to the first area of said diaper, said envelope being of sufficient size to accommodate said diaper in a disposal configuration and the mouth of said envelope being sufficiently large to accept said diaper when said diaper is swingably positioned into said envelope;
   strap means having a free end for securing the second section to the first section to position said diaper on a wearer in a use configuration and restricting the mouth of said envelope in the disposal configuration; and
   adhesive means mounted on said strap means proximate the free end for affixing the free end to the first section of said diaper in the use configuration and to said envelope in the disposal configuration.

6. The diaper assembly of claim 5 in which the second section of said diaper further includes a second area and said envelope has an attachment region which is removably attached to the second area of said diaper in the use configuration.

7. The diaper assembly of claim 5 in which said envelope includes means, disposed on the rim opposite the fixed portion, for guiding said strap means during restriction of the mouth of the envelope in the disposal configuration.

8. The diaper assembly of claim 7 in which said means for guiding is an opening in the rim of said envelope.

9. The diaper assembly of claim 5 in which the portion of the rim of said envelope which is fixed to the first area of said diaper is a portion of the interior surface of the rim.

10. The diaper assembly of claim 5 in which a portion of said strap means opposite the free end is fixed to the rim of said envelope.

11. The diaper assembly of claim 5 in which a portion of said strap means opposite the free end is fixed to the first area of said diaper.

12. The diaper assembly of claim 5 in which said strap means has at least two free ends.

13. The diaper assembly of claim 12 in which said envelope includes means, on either side of the fixed portion of the rim, for receiving each free end of said strap means.

14. The diaper assembly of claim 13 in which said means for receiving includes at least one slit in the envelope on either side of the fixed portion.

15. The diaper assembly of claim 5 in which the first area is located in the region of said diaper that is positionable near the waist of the wearer.

16. The diaper assembly of claim 5 further including a protective covering which overlies at least a portion of said envelope to restrict inadvertent movement of said envelope in the use configuration.

17. The diaper assembly of claim 5 in which the first section is the front of the diaper and the second section is the back of the diaper.

18. A diaper assembly with integral disposal system, comprising:

a diaper having an outer liner on which is defined a first section and a second section, the second section having a first area and a second area;

an envelope which has a mouth, said envelope having defined on it a rim surrounding the mouth, being swingably fixed along a portion of the rim to the first area of said diaper, and being removably attached to the second area of said diaper in a use configuration, said envelope being of sufficient size to accommodate said diaper in a disposal configuration and the mouth of said envelope being sufficiently large to accept said diaper when said diaper is swingably positioned into said envelope;

strap means having a free end for securing the second section to the front section to position said diaper on a wearer in the use configuration and restricting the mouth of the envelope in the disposal configuration; and adhesive means mounted on said strap means proximate the free end for affixing the free end to the first section of the diaper in the use configuration and to the envelope in the disposal configuration.

19. The diaper assembly of claim 18 in which said strap means has at least two free ends.

20. The diaper assembly of claim 1 in which said strap means has at least one free end and includes adhesive means mounted proximate said free end.

* * * * *

UNITED STATES PATENT AND TRADEMARK OFFICE
CERTIFICATE OF CORRECTION

PATENT NO.  : 4,604,096
DATED       : August 5, 1986
INVENTOR(S) : Raymond S. Dean et al.

It is certified that error appears in the above-identified patent and that said Letters Patent is hereby corrected as shown below:

On the Title page, Item [73] should read

-- Personal Hygiene Reseach Associates,
       Reading, Mass. --.

Signed and Sealed this
Ninth Day of December, 1986

*Attest:*

DONALD J. QUIGG

*Attesting Officer*      *Commissioner of Patents and Trademarks*